United States Patent [19]

Nishikido et al.

[11] 4,279,836
[45] Jul. 21, 1981

[54] HYDROXAMIC ACID DERIVATIVE AND METHOD OF PREPARING METOCLOPRAMIDE USING SAME

[75] Inventors: Joji Nishikido, Fuji; Yohei Fukuoka, Kurashiki; Nobuhiro Tamura, Chigasaki, all of Japan

[73] Assignee: Asahi Kasei Kogyo Kabushiki Kaisha, Osaka, Japan

[21] Appl. No.: 38,696

[22] Filed: May 14, 1979

[30] Foreign Application Priority Data

May 12, 1978 [JP] Japan ................................ 53/55675

[51] Int. Cl.³ .................. C07C 83/02; C07C 101/02; C07C 103/26
[52] U.S. Cl. ........................ 260/500.5 H; 260/453.8; 560/41; 560/42; 562/450; 562/451; 564/167
[58] Field of Search .... 260/453 RW, 559 A, 500.5 H, 260/453.8; 560/41, 42; 562/450, 451; 564/167

[56] References Cited

U.S. PATENT DOCUMENTS

| | | |
|---|---|---|
| 2,650,241 | 8/1953 | Weisblat et al. ........................ 560/41 |
| 2,772,281 | 11/1956 | Holly et al. .................... 260/500.5 H |
| 3,177,252 | 4/1965 | Thominet ................. 560/41 |

FOREIGN PATENT DOCUMENTS

| | | | |
|---|---|---|---|
| 1146333 | 4/1966 | United Kingdom ...................... 560/41 |
| 1153796 | 11/1966 | United Kingdom ...................... 560/41 |

OTHER PUBLICATIONS

Noller, Textbook of Organic Chemistry, W. B. Saunders Company, Philadelphia, 1958, p. 190.

Primary Examiner—Henry R. Jiles
Assistant Examiner—Robert C. Whittenbaugh
Attorney, Agent, or Firm—Finnegan, Henderson, Farabow, Garrett & Dunner

[57] ABSTRACT

2-Chloro-4-N-(β-diethylaminoethyl)aminocarbonyl-5-methoxybenzhydroxamic acid of the formula,

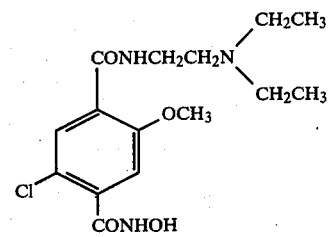

or its metal salt, a process for their preparation and a process for preparing metoclopramide of the formula,

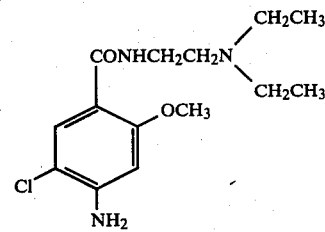

using the above described 2-chloro-4-N-(β-diethylaminoethyl)aminocarbonyl-5-methoxybenzhydroxamic acid or its metal salt.

19 Claims, No Drawings

HYDROXAMIC ACID DERIVATIVE AND METHOD OF PREPARING METOCLOPRAMIDE USING SAME

BACKGROUND OF THE INVENTION

1. Field of the Invention

This invention relates to a novel hydroxamic acid derivative and a method of preparing metoclopramide using the same.

2. Description of the Prior Art

Many methods are reported by preparing metoclopramide, i.e., N-(2-diethylaminoethyl)-2-methoxy-4-amino-5-chlorobenzamide useful as a antiemetic and an improving agent for digestion. Most of these methods use p-aminosalicylic acid as the starting material. More specifically, N-(2-diethylaminoethyl)-2-methoxy-4-amino-5-chlorobenzamide is prepared through each of the reaction steps including the methoxylation of the hydroxyl group at the 2-position of the benzene ring of the starting material, the chlorination at the 5-position of the benzene ring and the amidation of the carbonyl group with N,N-diethylethylenediamine.

One representative example of these conventional method is as follows;

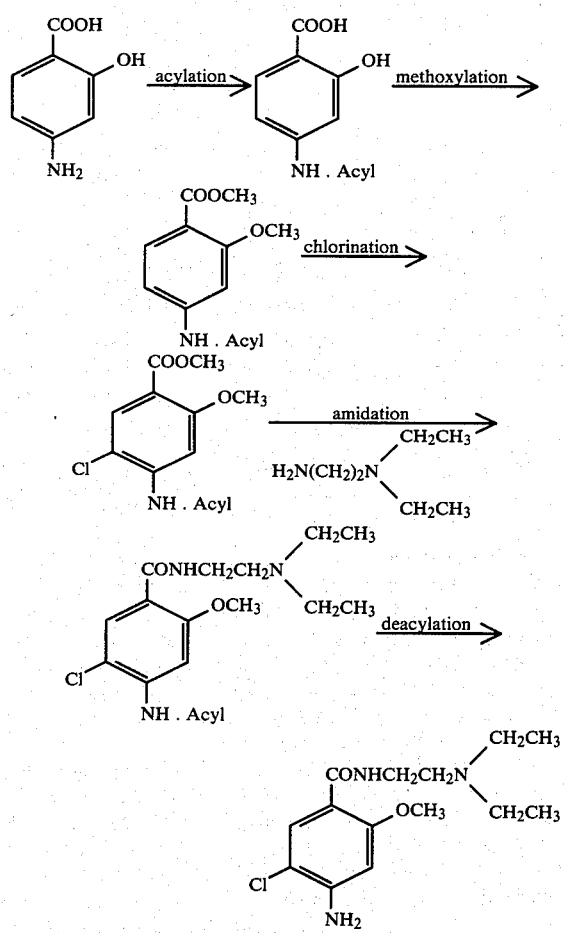

However, these conventional methods require complicated treatments in reaction, separation and purification of the above described steps and expensive reagents.

SUMMARY OF THE INVENTION

An object of this invention is to provide a novel hydroxamic acid derivative which can be used as a starting material for preparing metoclopramide and to provide a method of the production thereof.

Another object of this invention is to provide a method of preparing metoclopramide having high purity from the hydroxamic acid derivative.

Accordingly, the present invention in one embodiment provides 2-chloro-4-N-(β-diethylaminoethyl)aminocarbonyl-5-methoxybenzhydroxamic acid of the formula (I),

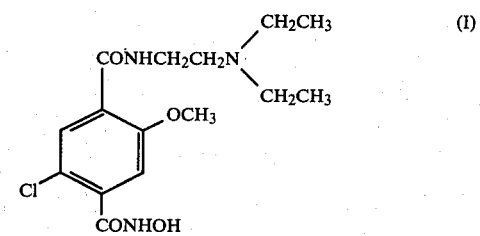

or its metal salt of the formula (II),

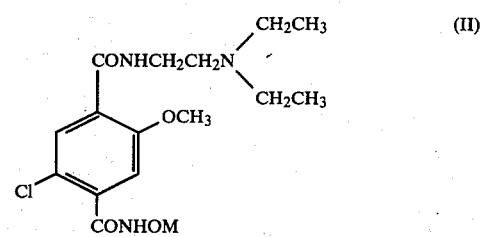

wherein M is an alkali metal or an alkaline earth metal.

The present invention in another embodiment provides a method of preparing N-(2-diethylaminoethyl)-2-methoxy-4-amino-5-chlorobenzamide of the formula (V),

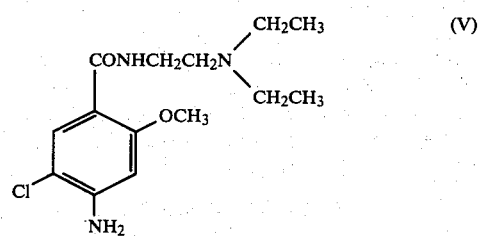

which comprises heating the compound of the formula (I) or the compound of the formula (II) as described above.

In a further embodiment, the present invention provides 2-chloro-4-N-(β-diethylaminoethyl)aminocarbonyl-5-methoxybenzoic acid or its alkyl ester of the formula (III),

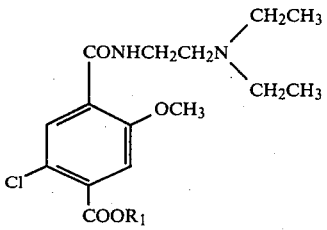

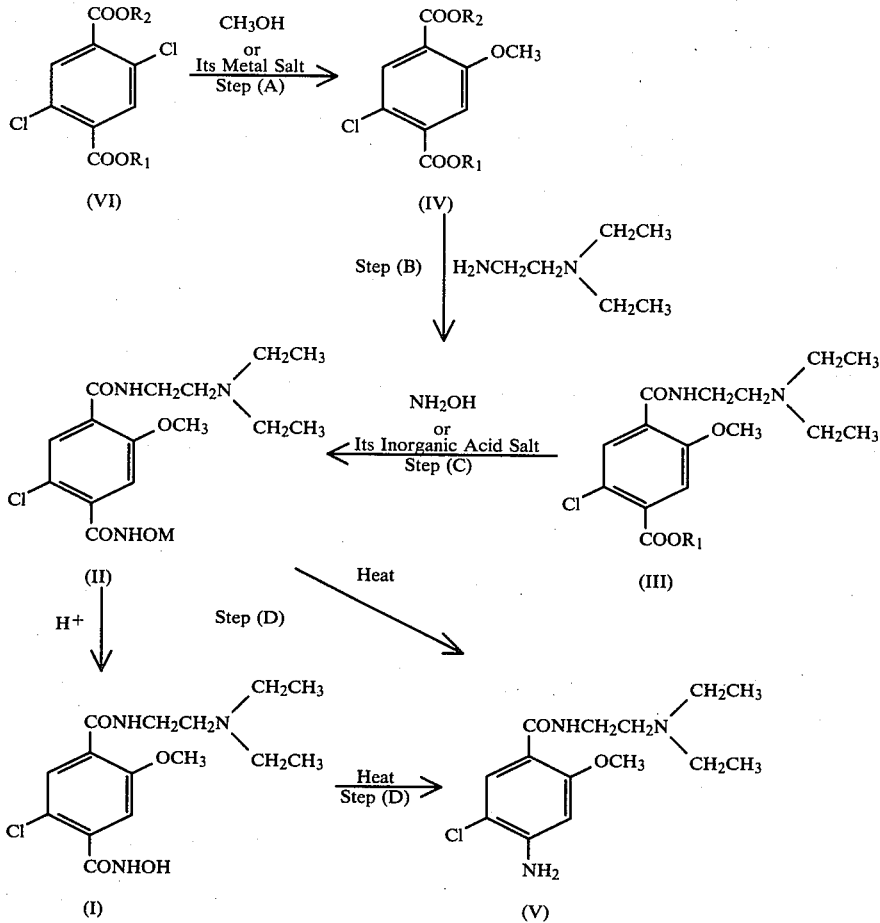

wherein $R_1$ is a hydrogen atom, a $C_{1-7}$ alkyl group or phenyl group.

In an even further embodiment, the invention provides a method of preparing the compound of the formula (I) or the compound of the formula (II) as described above which comprises reacting the compound of the formula (III) as described above with hydroxylamine or its inorganic acid salt.

DETAILED DESCRIPTION OF THE INVENTION

Suitable examples of M in the compound of the formula (II) as described above which can be employed in this invention include sodium metal, potassium metal, lithium metal, calcium metal, magnesium metal and barium metal. Of these metals, sodium metal and potassium metal are preferred.

Suitable examples of $R_1$ in the compound of the formula (III) as described above which can be employed in this invention include hydrogen atom, methyl group, ethyl group, n-propyl group, n-butyl group, isobutyl group, n-pentyl group and phenyl group. Of these groups, methyl group is preferred.

The method of preparing the compound of the formula (I) and the compound of the formula (II) as described above and the method of preparing metoclopramide of the formula (V) as described above from the compound of the formula (I) and the compound of the formula (II) will now be given.

In the above described formulae (I) to (V), $R_1$ and $R_2$ may be the same or different and represent a hydrogen atom, a phenyl group or a $C_{1-7}$ alkyl group but in case one of $R_1$ and $R_2$ is a hydrogen atom, the other of $R_1$ and $R_2$ is not a $C_{1-7}$ alkyl group, and M is an alkali metal or an alkaline earth metal.

The reaction conditions in each of steps (A) to (D) will now be explained.

The compound of the formula (VI) is known and can, for example, be easily obtained by reacting terephthalic acid with chlorine gas using iodine as a catalyst to form 2,5-dichloroterephthalic acid and, if desired, esterifying the 2,5-dichloroterephthalic acid with a $C_{1-7}$ alkyl alcohol such as methanol, ethanol, n-propanol, n-butanol, iso-butanol and n-pentanol. Since methanol is used in step (A), the esterification with methanol is especially preferred.

The amount of iodine which can be employed as the catalyst typically ranges from about 1 to about 5% by mole based on the mole of terephthalic acid.

In step (A) the known compound of the formula (IV) can be prepared by reacting the compound of the formula (VI) with methanol or a metal salt of methanol. When methanol is used, it is preferred to conduct the reaction in the presence of a catalyst including, for example, iodine, copper and copper iodide. Appropriate metal salts of methanol which can be employed in step (A) include alkali metal salts of methanol of which sodium methylate is preferred. In this step methanol is employed as a reaction medium. The weight ratio of methanol to the compound of the formula (VI) which can be employed in step (A) typically ranges from about 2 to about 100. A preferred weight ratio ranges from about 5 to about 30. The reaction temperature typically ranges from about 100° C. to about 200° C., and preferably from about 130° C. to about 160° C. and the reaction period of time typically ranges from about 3 to about 6 hours. The reaction pressure which can be employed typically ranges from about 3 Kg/cm$^2$ to about 40 Kg/cm$^2$.

The amidation reaction of step (B) for preparing the compound of the formula (III) can be conducted by reacting the compound of the formula (IV) with N,N-diethylethylenediamine without any reaction solvent or in the presence of an inert reaction medium under heating to give the compound of the formula (III) at high yields.

Suitable reaction media which can be employed in the step (B) include inert hydrocarbons such as benzene, toluene, xylene, n-pentane, n-hexane, cyclohexane and any mixtures thereof.

The weight ratio of the reaction medium to the compound of the formula (IV) which can be employed typically ranges from about 1 to about 100 and preferably from about 2 to about 50. The reaction temperature used typically ranges from about 50° C. to about 180° C. and a preferred reaction temperature ranges from about 80° C. to about 140° C. The reaction time typically ranges from about 1 to about 7 hours. The reaction pressure which can be employed typically ranges from atmospheric pressure to about 15 Kg/cm$^2$.

The amount of N,N-diethylethylenediamine which can be employed in the step (B) typically ranges from about 0.8 to about 3 moles and preferably from about 1.0 to about 1.5 moles per mole of the compound of the formula (IV).

The compound of the formula (III) is a novel compound and of use as a starting material for preparing the compound of the formula (I) or the compound of the formula (II) of this invention.

The reaction in step (C) for preparing the compound of the formula (I) or the compound of the formula (II) is to convert the compound (III) to the hydroxamic acid or its salt, respectively, using hydroxylamine or its inorganic acid salt such as the sulfate, hydrochloride, phosphate and borate as the reagent. Of these hydroxylamine and its inorganic salts which can be used as the reagents, hydroxylamine sulfate and hydroxylamine hydrochloride are preferred.

In preparing the compound of the formula (II), the reaction is conducted in the presence of an alkaline compound such as a hydroxide of an alkali metal or a hydroxide of n alkaline earth metal which firstly makes hydroxylamine free and secondly forms the salt of the hydroxamic acid of the formula (I). The compound of formula (I) can be prepared by neutralizing the metal salt of the hydroxamic acid with an inorganic acid such as hydrochloric acid and sulfuric acid.

Treating the compound of the formula (I) with an equimolar amount of an inorganic acid such as hydrochloric acid, sulfuric acid, phosphoric acid or boric acid, preferably hydrochloric acid, forms a compound of the following formula (VII):

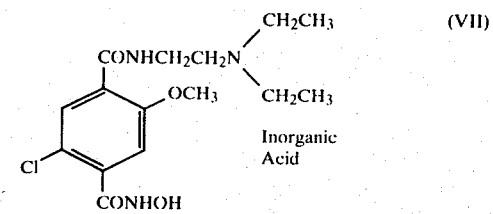

Specific examples of suitable hydroxides of an alkali metal of hydroxides of an alkaline earth metal include sodium hydroxide and potassium hydroxide. The hydroxide of an alkali metal or the hydroxide of an alkaline earth metal is in an amount sufficient to neutralize the inorganic acid salt of hydroxylamine and the hydroxamic acid group of the compound of the formula (I).

The amount of hydroxylamine or its inorganic acid salt which can be employed in the reaction of step (C) typically ranges from about 1 to about 6 and preferably from about 1.2 to about 3 moles per mole of 2-chloro-4-N-(β-diethylaminoethyl)aminocarbonyl-5-methoxybenzoic acid or its alkyl ester of the formula (III).

In general, the reaction of step (C) is conducted in the presence of a reaction medium. Any reaction media which do not change in the reaction can be employed in the reaction of step (C). Appropriate reaction media include methanol, ethanol, propanols, butanols, tetrahydrofuran, dioxane, chloroform, dichloroethane and any mixtures thereof. Of these reaction media, methanol, ethanol, tetrahydrofuran and dioxane are preferred. The weight ratio of the reaction medium to the compound of the formula (III) which can be employed in the reaction of step (C) typically ranges from about 1 to about 500. A preferred weight ratio ranges from about 5 to about 200.

The reaction temperature used typically ranges from about 5° C. to about 30° C. and the reaction time used typically ranges from about 1 to about 10 hours and preferably from about 3 to about 7 hours. The reaction can be typically carried out at atmospheric pressure.

For example, the reaction of step (C) can be conducted by dissolving or dispersing the compound of the formula (III) as the starting material and an inorganic acid salt of hydroxylamine in methanol as the reaction medium and adding dropwise a methanol solution of sodium hydroxide to the mixture over a period of one hour and further maintaining the reaction mixture at a temperature of about 5° C. to about 30° C. for about 3 to about 7 hours while freeing hydroxylamine.

2-Chloro-4-N-(β-diethylaminoethyl)aminocarbonyl-5-methoxybenzhydroxamic acid of the formula (I) and its metal salt of the formula (II) are novel compounds and of use as the starting materials for preparing metoclopramide of the formula (V).

Metoclopramide of the formula (V) can be prepared by subjecting the compound of the formula (I), (II) or (VII) to the thermal conversion reaction of step (D).

The compound of the formula (I), (II) or (VII) after removal of the inorganic acid salt from the reaction mixture obtained in step (C) can be subjected to the thermal conversion reaction of step (D). Also, the reaction mixture obtained in step (C) as such without recovering and purifying the reaction product or if necessary or if desired after separating the reaction medium can be subjected to the thermal conversion reaction of step (D). In case of the compound of the formula (VII) as the starting material the reaction product is neutralized with an alkali.

The thermal conversion reaction of step (D) is typically conducted at a temperature of about 130° C. to about 250° C. A preferred temperature ranges from about 150° C. to about 230° C. The pressure of the thermal conversion reaction which can be employed typically ranges from about 2 Kg/cm$^2$ to about 80 Kg/cm$^2$.

The thermal conversion reaction may be conducted either in the absence or presence of an organic reaction medium. Any organic reaction media which do not change in the thermal conversion reaction can be used in this reaction.

Specific examples of suitable organic reaction media include, benzene, toluene, xylene, tetrahydrofuran, dioxane, methanol, ethanol, propanols, butanols, pentanols, pyridine, N,N-dimethylformamide, N,N-dimethylacetamide, dimethyl sulfoxide, acetonitrile, propionitrile, benzonitrile and any mixtures thereof.

The amount of the organic reaction medium may vary depending on its type selected and the thermal conversion reaction temperature employed. The weight ratio of the organic reaction medium to the compound of the formula (I) or the compound of the formula (II) typically ranges from about 1 to about 400 and preferably from about 2 to about 100.

The thermal conversion reaction time may vary depending on the reaction temperature employed and typically ranges from about 0.5 to about 10 hours. A preferred reaction time ranges from about 1 to about 5 hours.

Further, in order to prevent the desired product from discoloring it is preferred that the thermal conversion reaction is conducted in an inert atmosphere such as nitrogen.

When the compound of the formula (II) is subjected to the thermal conversion reaction in step (D), the metal of the formula (II) is freed from the compound of the formula (II), and the metoclopramide obtained is, in general, recrystallized from methanol. The metal thus freed can be separated from the metoclopramide in the recrystallization.

According to this invention, each of the above described steps (A) to (D) proceeds at high yields and high selectivities, and the products can be easily separated and purified, resulting in the desired products having high purity. Also, each of steps (A) to (D) can be succeeded by the subsequent step without separation nor purification of the products.

Thus, the method of this invention can give the desired products having higher purity at a lower cost than the conventional methods and is desirable from the industrial viewpoint.

The following Examples are given to illustrate the present invention more specifically. However, it should be understood that the invention is in no way limited by these Examples.

EXAMPLE 1

In a 200 cc autoclave were charged 26 g of dimethyl 2,5-dichloroterephthalate, 6.5 g of sodium methylate and 100 g of methanol, and the reaction was conducted at 150° C. for 5 hours. After the reaction, the reaction mixture solution was cooled to room temperature and filtered. Part of methanol was distilled off from the filtrate and then the remaining solution was condensed and left to stand at 10° C. for 5 hours for cooling to precipitate white needle-like crystals. These crude crystals were separated and recrystallized from methanol to give 19 g of needle-like crystals of dimethyl 2-chloro-5-methoxyterephthalate having the following elemental analysis values.

Elemental Analysis Values: Calculated (%): C, 51.07; H, 4.26; O, 30.95;

Found (%): C, 51.03; H, 4.22; O, 30.67

In a 200 cc autoclave were placed 19 g of the dimethyl 2-chloro-5-methoxyterephthalate as obtained in the above described step, 8.7 g of N,N-diethylethylenediamine and 100 g of xylene and the reaction was conducted in a nitrogen atmosphere at 90° C. for 2 hours and further at 130° C. for 3 hours. After completion of the reaction, the xylene in the reaction mixture solution was distilled off under reduced pressure. The residue was added with methanol, dissolved therein under heating, added with hydrochloric acid and left to stand at room temperature for 6 hours for cooling to precipitate white needle-like crystals. These crystals were separated by filtration and dried to give 23.6 g of methyl 2-chloro-4-N-(β-diethylaminoethyl)aminocarbonyl-5-methoxy benzoate hydrochloride having the following infrared absorption spectrum and elemental analysis values.

Infrared Absorption Spectrum: 3350 cm$^{-1}$ and 1640 cm$^{-1}$; —CONH—; 2980 cm$^{-1}$ and 2950 cm$^{-1}$; —CH$_2$—, —CH$_2$CH$_3$; 2500-2730 cm$^{-1}$; ammonium salt; 1730 cm$^{-1}$; —COOCH$_3$ Elemental Analysis Values: Calculated (%): C, 50.79; H, 6.08; N, 7.41; O, 16.93; Found (%): C, 50.61; H, 6.10; N, 7.38; O, 16.95

The methyl 2-chloro-4-N-(β-diethylaminoethyl)aminocarbonyl-5-methoxy benzoate hydrochloride was treated with a sodium hydroxide aqueous solution to free the hydrochloric acid and then subjected to NMR spectral analysis. NMR Spectrum (in CD$_3$Cl at 20° C.):

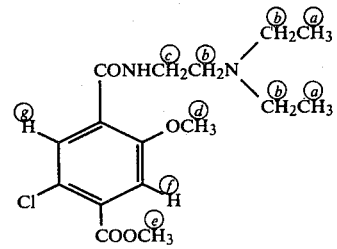

Chemical shifts of above described protons:
H(a)=1.11 (PPM)
H(b)=2.64
H(c)=3.76
H(d)=3.98
H(e)=4.02
H(f)(g)=7.35–8.21

In 100 g of methanol were added 10 g of the dimethyl 2-chloro-4-N-(β-diethylaminoethyl)aminocarbonyl-5-methoxybenzoate hydrochloride as obtained in the above described step and 2.8 g of hydroxylamine hydrochloride, and to the mixture was added dropwise with vigorous agitation 100 g of a methanol solution in which 5.8 g of potassium hydroxide had been dissolved, over a period of 60 minutes at a temperature of 5° C. to 10° C. and vigorous agitation was further continued for 3 hours at a temperature of 5° C. to 10° C. in a nitrogen atmosphere. After completion of the reaction, the reaction mixture solution was filtered to remove the inorganic salt, and part of methanol was distilled off from the filtrate and the remaining filtrate was concentrated and left to stand for cooling to precipitate white crystals. The yield of crystals was 8.2 g. These crystals were confirmed to be potassium 2-chloro-4-N-($\beta$-diethylaminoethyl)aminocarbonyl-5-methoxybenzhydroxamate from the following results of infrared absorption spectral analysis, elemental analysis and NMR spectral analysis.

Infrared Absorption Spectrum: 3200–3400 cm$^{-1}$ (—CONH—); 2800–2980 cm$^{-1}$ (—CH$_2$—, —CH$_2$CH$_3$); 1640–1650 cm$^{-1}$ (—CONH—); 1600 cm$^{-1}$; (benzene nucleus); 1240 cm$^{-1}$; (—OCH$_3$);

Elemental Analysis Values: Calculated (%): C, 47.24; H, 5.51; N, 11.02; O, 16.80; Found (%): C, 47.29; H, 5.50; N, 11.07; O, 16.86

NMR Spectrum (in CD$_3$Cl at 20° C.):

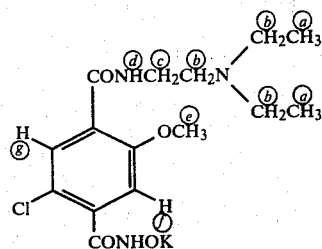

Chemical shifts of protons as described above
H$_{(a)}$=0.96–1.11 (PPM)
H$_{(b)}$=2.44–2.67
H$_{(c)}$=3.39–3.55
H$_{(d)}$=6.86
H$_{(e)}$=3.91
H$_{(f)(g)}$=7.80–8.20

In an autoclave flashed with nitrogen, 8.2 g of the potassium 2-chloro-4-N-($\beta$-diethylaminoethyl)aminocarbonyl-5-methoxybenzhydroxamate as obtained in the above described step with 30 ml of toluene were heated at 180° C. for 2 hours with agitation to conduct the thermal conversion reaction.

The reaction solution was taken out of the autoclave and the toluene was distilled off. Then the product was treated with a small amount of active carbon and recrystallized from methanol to give 5.2 g of white needle-like crystals.

These crystals are identified as metoclopramide in comparison with the commercially available standard compound by NMR, ultraviolet absorption spectral analysis, infrared absorption spectral analysis and mass spectral analysis and melting point measurement. NMR: Chemical shifts were as follows.

| | White Needle-like Crystals | | Standard Compound |
|---|---|---|---|
| PPM | 8.06 | PPM | 8.06 |
| | 6.26 | | 6.26 |
| | 4.41 | | 4.43 |
| | 3.89 | | 3.84 |
| | 3.56 | | 3.50 |
| | 3.47 | | 3.43 |
| | 2.65 | | 2.60 |
| | 2.57 | | 2.55 |
| | 1.03 | | 1.04 |

Ultraviolet Absorption Spectrum: (Measured using 100% methanol solution. The maximum and minimum absorptions were in accord with those of the standard compound.)

| Maximum Absorption (m$\mu$) | Minimum Absorption (m$\mu$) |
|---|---|
| 308 | 291 |
| 274 | 251 |
| 230 | |
| 213 | |

Infrared Absorption Spectrum: (Measured by the KBr disk method. Each of the absorption were numbers was in accord with that of the standard compound.)

| 3200–3400 cm$^{-1}$ | 3 Absorptions (—NH$_2$, —CONH—) |
|---|---|
| 2800–2960 cm$^{-1}$ | 5 Absorptions (CH$_2$—CH$_2$—N(C$_2$H$_5$)(C$_2$H$_5$)) |
| 1645 cm$^{-1}$ | 1 Absorption (—CON—) |
| 1637 cm$^{-1}$ | 1 Absorption (—CON—) |
| 1595 cm$^{-1}$ | 1 Absorption (benzene nucleus) |

Mass Spectrum: (The molecular weight was 299 and each fragment as shown below was all in accord with that of the standard compound.) Fragment: 270, 227, 201, 184, 167, 100, 99, 86, ....

Melting Point: 145°–146° C. (Standard Compound: 147° C.)

From the above described results the white needle-like crystals were confirmed to be metoclopramide.

EXAMPLE 2

In a 200 cc autoclave were charged 20 g of the dimethyl 2-chloro-5-methoxyterephthalate as obtained in the first step of Example 1, 9 g of N,N-diethylethylenediamine and 100 g of toluene and the reaction was conducted in a nitrogen atmosphere at 100° C. for 2 hours and further at 140° C. for 2 hours. After completion of the reaction, the toluene was distilled off from the reaction mixture solution to give 25.2 g of crude methyl 2-chloro-4-N-($\beta$-diethylaminoethyl)aminocarbonyl-5-methoxybenzoate. In 200 g of methanol were added 25.2 g of the methyl 2-chloro-4-N-($\beta$-diethylaminoethyl)aminocarbonyl-5-methoxybenzoate thus obtained and 7.3 g of hydroxylamine hydrochloride, and 150 g of a methanol solution in which 10.6 g of potassium hydroxide had been dissolved were added dropwise to the mixture at a temperature of 5° C. to 10° C. with stirring over a period of 30 minutes and the mixture was further stirred for 4 hours at a temperature of 5° C. to 10° C. in a nitrogen atmosphere. After completion of the reaction, the potassium chloride precipitated was separated by filtration and the filtrate was charged in an autoclave and the thermal conversion reaction was further continued at 190° C. for one hour.

After completion of the reaction, the reaction solution was treated with a small amount of active carbon and part of methanol was distilled off, and then the reaction solution was concentrated and left to stand for cooling for 24 hours to give 16.2 g of white needle-like crystals. These crystals were confirmed to be metoclopramide by the same identification method as in Example 1.

On the other hand, after part of methanol was distilled off from the filtrate obtained by separating the potassium chloride precipitated from the reaction mixture solution, the solution thus obtained was left to stand for cooling at 5° C. for 10 hours to give white crystals. These crystals were confirmed to be potassium 2-chloro-4-N-(β-diethylaminoethyl)aminocarbonyl-5-methoxybenzhydroxamate from the following results of infrared absorption spectral analysis, elemental analysis and NMR spectral analysis.

Infrared Absorption Spectrum: 3200–3400 cm$^{-1}$ (—CONH—); 2800–2980 cm$^{-1}$ (—CH$_2$—, —CH$_2$CH$_3$); 1640–1650 cm$^{-1}$ (—CONH—); 1600 cm$^{-1}$ (benzene nucleus); 1240 cm$^{-1}$ (—OCH$_3$);

Elemental Analysis Values: Calculated (%): C, 47.24; H, 5.51; N, 11.02; O, 16.80; Found (%): C, 47.30; H, 5.46; N, 11.09; O, 16.84

NMR Spectrum (in CD$_3$Cl at 20° C.):

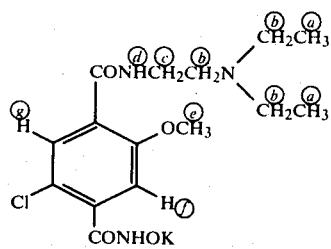

H$_{(a)}$=0.96–1.10 (PPM)
H$_{(b)}$=2.44–2.67
H$_{(c)}$=3.39–3.55
H$_{(d)}$=6.84
H$_{(e)}$=3.93
H$_{(f)(g)}$=7.80–8.20

EXAMPLE 3

In a 200 cc autoclave were 20 g of dimethyl 2-chloro-5-methoxyterephthalate in the first step of Example 1, 9 g of N,N-diethylethylenediamine and 100 g of toluene and the reaction was conducted at 80° C. for 2 hours in a nitrogen atmosphere and further continued at 150° C. for one hour. After completion of the reaction, the toluene was distilled off from the reaction solution to give 23.9 g of crude methyl 2-chloro-4-N-(β-diethylaminoethyl)aminocarbonyl-5-methoxybenzoate. In 200 g of methanol were added 23.9 g of the methyl 2-chloro-4-N-(β-diethylaminoethyl)aminocarbonyl-5-methoxybenzoate thus obtained and 7.3 g of hydroxylamine hydrochloride, and to the mixture were added dropwise 150 g of a methanol solution in which 10 g of potassium hydroxide had been dissolved, at a temperature of 5° C. to 10° C. with stirring over a period of 30 minutes, and the reaction was further continued for 4 hours at a temperature of 5° C. to 10° C. in a nitrogen atmosphere. After completion of the reaction, the potassium chloride precipitated was separated by filtration and the filtrate was neutralized with hydrochloric acid and then the solvent was distilled off. The residue and 100 ml of dioxane were placed in an autoclave and the thermal conversion reaction was conducted at 180° C. for one hour with stirring. After completion of the reaction, the reaction mixture solution was made alkaline by addition of a methanol solution of potassium hydroxide and after removal of the inorganic salt, the reaction solution was treated with a small amount of active carbon, then concentrated and left to stand for cooling to give 15.2 g of white needle-like crystals of metoclopramide.

On the other hand, prior to the thermal conversion reaction in dioxane, the filtrate obtained by separating the potassium chloride precipitated from the reaction mixture solution was neutralized and a small amount of methanol was distilled off. Then the solution was left to stand for cooling at 5° C. for 15 hours to give white crystals. These crystals were confirmed to be 2-chloro-4-N-(β-diethylaminoethyl)aminocarbonyl-5-methoxybenzhydroxamic acid hydrochloride from the following results of infrared absorption spectral analysis, elemental analysis and NMR spectral analysis.

Infrared Absorption Spectrum: 3220–3440 cm$^{-1}$ (—CONH—); 2800–2980 cm$^{-1}$ (—CH$_2$—, —CH$_2$CH$_3$); 2500–2740 cm$^{-1}$ (ammonium hydrochloride); 1640–1660 cm$^{-1}$ (—CONH—); 1230 cm$^{-1}$ (—OCH$_3$);

Elemental Analysis Values: Calculated (%): C, 47.49; H, 6.07; N, 11.08; O, 16.89; Found (%): C, 47.53; H, 6.03; N, 11.13; O, 16.81

NMR Spectrum (in D$_2$O at 20° C.):

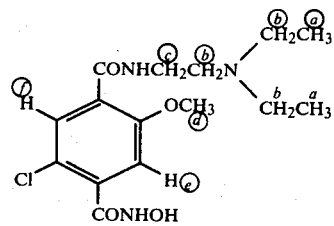

Chemical shifts of above described protons:
H$_{(a)}$=1.40–1.55 (PPM)
H$_{(b)}$=3.37–3.58
H$_{(c)}$=3.86–4.00
H$_{(d)}$=4.02
H$_{(e)(f)}$=7.84–8.15

EXAMPLE 4

In a 300 cc autoclave were charged 20 g of the dimethyl 2-chloro-5-methoxyterephthalate as obtained in Example 1, 11 g of N,N-diethylethylenediamine and 200 g of cyclohexane and the reaction was conducted at 70° C. for 3 hours and further at 130° C. for 2 hours in a nitrogen atmosphere. After completion of reaction, the cyclohexane and excess N,N-diethylethylenediamine were distilled off from the reaction mixture under reduced pressure to give 25.4 g of crude 2-chloro-4-N-(β-diethylaminoethyl)aminocarbonyl-5-methoxybenzoate. In a mixture of 100 g of dioxane and 150 g of ethanol were added 2.54 g of the methyl 2-chloro-4-N-(β-diethylaminoethyl)aminocarbonyl-5-methoxybenzoate thus obtained and 29 g of hydroxylamine sulfate, and 100 g of ethanol solution in which 12 g of sodium hydroxide had been dissolved were added dropwise to the mixture at a temperature of 5° C. to 10° C. with stirring over a period of 30 minutes and the mixture thus obtained was further stirred at a temperature of 5° C. to 10° C. in a nitrogen atmosphere. After completion of the reaction, the sodium sulfate precipitated was separated by filtration and the filtrate was charged in an autoclave and the thermal conversion reaction was conducted at 160° C. for 5 hours with stirring. After completion of the reaction, the reaction solution was treated with a small amount of active carbon and the solvent was distilled off. Then the residue was dissolved in 80 g of methanol under heating and left to stand for cooling at 5° C. for 24 hours to give 15.0 g of white needle-like crystals. These crystals were confirmed to be metoclopramide by the same identification method as in Example 1.

On the other hand, after the solvent was distilled off from the filtrate obtained by separating the sodium sulfate precipitated from the reaction mixture solution, the residue was dissolved in 100 g of methanol under heating at 50° C. and the solution was left to stand for cooling at 5° C. for 10 hours to give white crystals. These crystals were confirmed to be sodium 2-chloro-4-N-($\beta$-diethylaminoethyl)aminocarbonyl-5-methoxybenzhydroxamate from the following results of infrared absorption spectral analysis, elemental analysis and NMR spectral analysis.

Infrared Absorption Spectrum: 3200–3400 cm$^{-1}$ (—CONH—); 2800–2980 cm$^{-1}$ (—CH$_2$, —CH$_2$CH$_3$); 1640–1650 cm$^{-1}$ (—CONH—); 1600 cm$^{-1}$ (benzene nucleus); 1240 cm$^{-1}$ (—OCH$_3$);

Elemental Analysis Values: Calculated (%): C, 49.32; H, 5.75; N, 11.51; O, 17.53; Found (%): C, 49.29; H, 5.71; N, 11.49; O, 17.60

NMR Spectrum (in CD$_3$Cl at 20° C.)

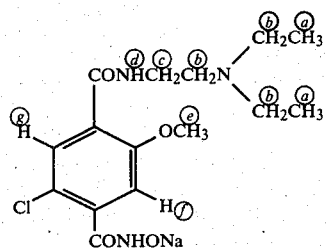

Chemical shifts of above described protons:
H$_{(a)}$=0.98–1.11 (PPM)
H$_{(b)}$=2.47–2.68
H$_{(c)}$=3.40–3.55
H$_{(d)}$=6.92
H$_{(e)}$=3.93
H$_{(f)(g)}$=7.82–8.21

EXAMPLE 5

In a mixture of 70 g of chloroform and 150 g of methanol were added 25 g of the crude methyl 2-chloro-4-N-($\beta$-diethylaminoethyl)aminocarbonyl-5-methoxybenzoate as obtained in Example 4 and 6.1 g of hydroxylamine hydrochloride, and to the mixture thus prepared were added dropwise 150 g of methanol solution in which 9 g of potassium hydroxide had been dissolved, at a temperature of 5° C. to 10° C. with stirring over a period of one hour and the reaction was further continued for 6 hours at a temperature of 5° C. to 10° C. in a nitrogen atmosphere. After completion of the reaction, the potassium chloride precipitated was separated by filtration and the filtrate was neutralized with hydrochloric acid and then the solvent was distilled off. The residue and 100 ml of acetonitrile were placed in an autoclave and the thermal conversion reaction was conducted at 160° C. for 2 hours with stirring. After completion of the reaction the acetonitrile was distilled off from the reaction mixture solution and the residue thus obtained was recrystallized from methanol to give 14.8 g of white needle-like crystals of metoclopramide.

On the other hand, after the filtrate obtained by separating the potassium chloride precipitated from the reaction mixture solution was neutralized, the solvent was distilled off from the filtrate and the residue was dissolved in 180 g of methanol under heating at 50° C. and the solution was left to stand for cooling at 5° C. for 15 hours to give white crystals. These crystals were confirmed to be 2-chloro-4-N-($\beta$-diethylaminoethyl)aminocarbonyl-5-methoxybenzhydroxamic acid hydrochloride by the same identification methods as in Example 3.

EXAMPLE 6

In a 200 cc autoclave were charged 20 g of the dimethyl 2-chloro-5-methoxyterephthalate as obtained in the first step of Example 1, 17 g of N,N-diethylethylenediamine and 100 g of n-hexane and the reaction was conducted at 100° C. for 4 hours in a nitrogen atmosphere. After completion of the reaction, the n-hexane and excess N,N-diethylethylenediamine were distilled off from the reaction mixture solution under reduced pressure to give 25 g of crude methyl 2-chloro-4-N-($\beta$-diethylaminoethyl)aminocarbonyl-5-methoxybenzoate. In a mixture of 200 g of methanol and 100 g of tetrahydrofuran were added 25 g of the methyl 2-chloro-4N-($\beta$-diethylaminoethyl)aminocarbonyl-5-methoxybenzoate thus obtained and 13 g of hydroxylamine hydrochloride, and 100 g of a methanol solution in which 9.7 g of calcium hydroxide had been dissolved were added dropwise to the mixture at a temperature of 5° C. to 10° C. with stirring over a period of one hour and the mixture thus obtained was further stirred for 7 hours at a temperature of 5° C. to 10° C. in a nitrogen atmosphere. After completion of the reaction, the reaction mixture solution obtained was charged in an autoclave and the thermal conversion reaction was conducted at 180° C. for 2 hours with stirring. After completion of the reaction, the inorganic salt precipitated was separated by filtration and the filtrate was treated with a small amount of active carbon and part of methanol was distilled off. The reaction solution thus obtained was concentrated and left to stand for cooling for 24 hours to give 14.9 g of white needle-like crystals of metoclopramide.

On the other hand, the reaction solution obtained by the reaction between methyl 2-chloro-4-N-($\beta$-diethylaminoethyl)aminocarbonyl-5-methoxybenzoate and hydroxylamine hydrochloride was neutralized with hydrochloric acid and the inorganic salt formed was separated by filtration. Then the filtrate was left to stand for cooling at 5° C. for 14 hours to give white crystals. These crystals were confirmed to be 2-chloro-4-N-($\beta$-diethylaminoethyl)aminocarbonyl-5-methoxybenzhydroxamic acid hydrochloride by the same identification methods as in Example 3.

EXAMPLE 7

10 g of the potassium 2-chloro-4-N-($\beta$-diethylaminoethyl)aminocarbonyl-5-methoxybenzhydroxamate as obtained in Example 1 were heated at 230° C. for 30 minutes in a nitrogen atmosphere. The reaction product was dissolved in methanol and insoluble substance were separated by filtration. Then the filtrate was treated with active carbon and left to stand for cooling to give 6.1 g of white needle-like crystals of metoclopramide.

EXAMPLE 8

10 g of the potassium 2-chloro-4-N-(β-diethylaminoethyl)aminocarbonyl-5-methoxybenzhydroxamate as obtained in Example 1 was heated in a solvent as set forth in Table at 170° C. for 2 hours in a nitrogen atmosphere. After completion of the reaction, the solvent was distilled off from the reaction mixture solution and the residue was dissolved in methanol and insoluble substances were separated by filtration. Then the filtrate was treated with active carbon and left to stand for cooling to give white needle-like crystals of metoclopramide in an amount as set forth in Table below.

TABLE

| Solvent | (g) | Metoclopramide (g) |
| --- | --- | --- |
| Toluene | 150 | 5.7 |
| N,N-Dimethylformamide | 50 | 5.4 |
| Pyridine | 50 | 6.0 |

While the invention has been described in detail and with reference to specific embodiments thereof, it will be apparent to one skilled in the art that various changes and modifications can be made therein without departing from the spirit and scope thereof.

What is claimed is:

1. 2-Chloro-4-N-(β-diethylaminoethyl)aminocarbonyl-5-methoxybenzhydroxamic acid of the formula (I),

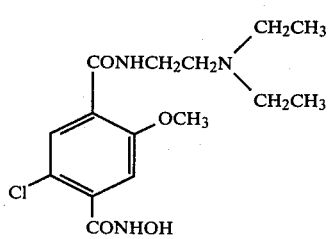

or its metal salt of the formula (II),

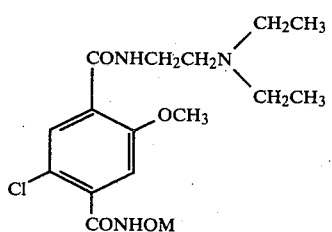

wherein M is an alkali metal or an alkaline earth metal.

2. The compound of the formula (II) of claim 1, wherein M is a metal selected from the group consisting of sodium, potassium, lithium, calcium, magnesium and barium.

3. The compound of the formula (II) of claim 2, wherein M is sodium or potassium.

4. 2-Chloro-4-N-(β-diethylaminoethyl)aminocarbonyl-5-methoxybenzoic acid or its ester of the following formula (III)

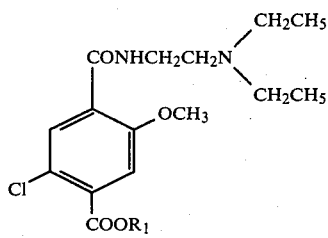

wherein $R_1$ is a hydrogen atom, a phenyl group or a $C_{1-7}$ alkyl group.

5. The compound of formula (III) of claim 4, wherein $R_1$ is a $C_{1-7}$ alkyl group selected from the group consisting of methyl, ethyl, n-propyl group, n-butyl group, isobutyl group and n-pentyl group.

6. A method of preparing metoclopramide of the formula (V),

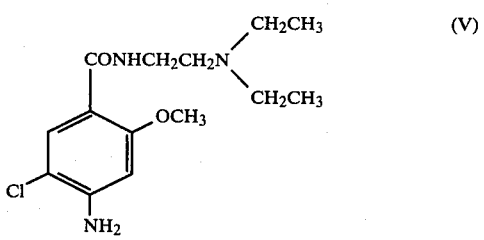

which comprises heating 2-chloro-4-N-(β-diethylaminoethyl)aminocarbonyl-5-methoxybenzhydroxamic acid of the formula (I) or its metal salt of the formula (II).

7. A method of preparing metoclopramide of the formula (V) which comprises treating 2-chloro-4N-(β-diethylaminoethyl)aminocarbonyl-5-methoxybenzhydroxamic acid of the formula (I) with an inorganic acid to give a compound of the formula (VII),

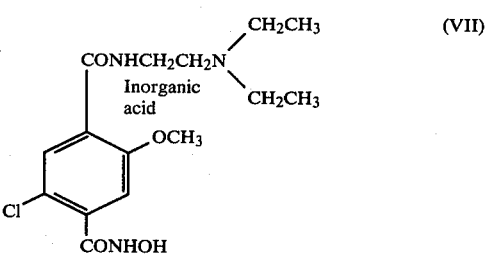

heating the compound of the formula (VII) and neutralizing the reaction product with an alkali.

8. The method of claim 7, wherein the inorganic acid is sulfuric acid, phosphoric acid, boric acid or hydrochloric acid.

9. The method of claim 8, wherein the inorganic acid is hydrochloric acid.

10. The method of claim 6, wherein the heating temperature ranges from about 130° C. to about 250° C.

11. The method of claim 10, wherein the heating temperature ranges from about 150° C. to about 230° C.

12. The method of claim 6, wherein the heating is conducted in the presence of an organic solvent which does not change in the thermal conversion reaction.

13. The method of claim 6, wherein the weight ratio of the organic solvent to the 2-chloro-4-N-(β-diethylaminoethyl)aminocarbonyl-5-methoxybenzhydroxamic acid of the formula (I) or its metal salt of the formula (II) ranges from about 1 to about 400.

14. The method of claim 13, wherein the weight ratio of the organic solvent to the 2-chloro-4-N-($\beta$-diethylaminoethyl)aminocarbonyl-5-methoxybenzhydroxamic acid of the formula (I) or its metal salt of the formula (II) ranges from about 2 to about 100.

15. The method of claim 6, wherein the heating is conducted in an inert gas atmosphere.

16. The method of claim 15, wherein the inert gas is nitrogen.

17. A method of preparing 2-chloro-4-N-($\beta$-diethylaminoethyl)aminocarbonyl-5-methoxybenzoic acid or its ester of the formula (III) which comprises reacting the compound of the formula (IV),

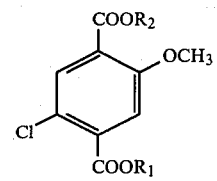

wherein $R_1$ and $R_2$ may be the same or different and represent a hydrogen atom, a phenyl group or a $C_{1-7}$ alkyl group but in case of one of $R_1$ and $R_2$ being a hydrogen atom the other of $R_1$ and $R_2$ is not a $C_{1-7}$ alkyl group, with N,N-diethylethylenediamine under heating, the amount of N,N-diethylethylenediamine ranging from about 0.8 mole to about 3 moles per mole of the compound of formula (IV), and the reaction temperature ranging from about 50° C. to about 180° C.

18. The method of claim 17, wherein the reaction temperature ranges from about 80° C. to about 140° C.

19. The method of claim 17, wherein the amount of N,N-diethylethylenediamine ranges from about 1.0 mole to about 1.5 moles per mole of the compound of the formula (IV).

* * * * *

UNITED STATES PATENT AND TRADEMARK OFFICE
CERTIFICATE OF CORRECTION

PATENT NO. : 4,279,836   Page 1 of 2
DATED : July 21, 1981
INVENTOR(S) : Joji Nishikido et al.

It is certified that error appears in the above—identified patent and that said Letters Patent is hereby corrected as shown below:

Claim 4, column 16, change the equation from

" 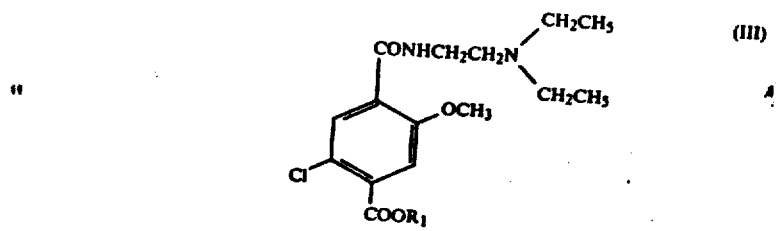

to

-- 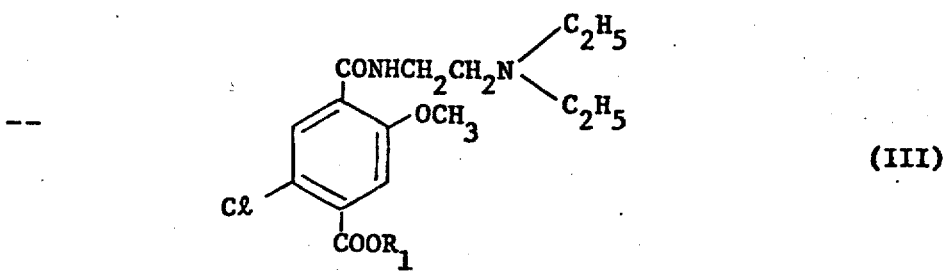

UNITED STATES PATENT AND TRADEMARK OFFICE
CERTIFICATE OF CORRECTION

PATENT NO. : 4,279,836

DATED : July 21, 1981

INVENTOR(S) : Joji Nishikido et al.

It is certified that error appears in the above—identified patent and that said Letters Patent is hereby corrected as shown below:

Claim 7, line 2, change "2-chloro-4N-($\beta$-" to --2-chloro-4-N-($\beta$- --.

Signed and Sealed this

Twenty-seventh Day of October 1981

[SEAL]

Attest:

GERALD J. MOSSINGHOFF

*Attesting Officer*     *Commissioner of Patents and Trademarks*